(12) United States Patent
Cole et al.

(10) Patent No.: US 7,763,021 B2
(45) Date of Patent: Jul. 27, 2010

(54) INTRAMEDULLARY NAIL ASSEMBLY

(75) Inventors: Dean J Cole, Orlando, FL (US); Michael Barker, Leeds (GB); Henri Defossez, Colombier (CH); Grant Mellor, Berwick (AU); James Brooks, Ilkley (GB)

(73) Assignee: Depuy International Limited (GB)

( * ) Notice: Subject to any disclaimer, the term of this patent is extended or adjusted under 35 U.S.C. 154(b) by 325 days.

(21) Appl. No.: 10/557,164

(22) PCT Filed: May 17, 2004

(86) PCT No.: PCT/GB2004/002110
§ 371 (c)(1),
(2), (4) Date: Nov. 9, 2006

(87) PCT Pub. No.: WO2004/100810
PCT Pub. Date: Nov. 25, 2004

(65) Prior Publication Data
US 2007/0100343 A1    May 3, 2007

(30) Foreign Application Priority Data
May 17, 2003 (GB) ............................. 0311373.5
Mar. 25, 2004 (GB) ............................. 0406823.5

(51) Int. Cl.
*A61B 17/56* (2006.01)
*A61B 17/58* (2006.01)
(52) U.S. Cl. ........................................................ 606/64
(58) Field of Classification Search ................ 606/67, 606/64, 61, 62, 66
See application file for complete search history.

(56) References Cited

U.S. PATENT DOCUMENTS

| 2,393,694 | A  | * | 1/1946  | Kirschner ..................... 606/59 |
| 5,441,500 | A  |   | 8/1995  | Seidel et al. |
| 5,472,444 | A  | * | 12/1995 | Huebner et al. ............... 606/64 |
| 5,658,287 | A  |   | 8/1997  | Hofmann et al. |
| 5,743,908 | A  | * | 4/1998  | Kim ............................ 606/64 |
| 6,168,595 | B1 | * | 1/2001  | Durham et al. ............... 606/64 |
| 6,221,074 | B1 | * | 4/2001  | Cole et al. ..................... 606/62 |
| 6,926,719 | B2 | * | 8/2005  | Sohngen et al. .............. 606/64 |
| 2002/0151898 | A1 | * | 10/2002 | Sohngen et al. .............. 606/62 |
| 2002/0156473 | A1 |   | 10/2002 | Bramlet et al. |
| 2003/0114855 | A1 | * | 6/2003  | Wahl et al. .................... 606/67 |
| 2006/0173457 | A1 | * | 8/2006  | Tornier ........................ 606/62 |

FOREIGN PATENT DOCUMENTS

| DE | 19960507 A1 | 6/2001 |
| EP | 0306709 A2  | 3/1989 |
| EP | 1175872 A2  | 1/2002 |
| EP | 1415604 A1  | 5/2004 |

* cited by examiner

Primary Examiner—Eduardo C Robert
Assistant Examiner—Ellen C Hammond

(57) ABSTRACT

An intramedullary nail assembly comprises an intramedullary nail component (2) al, the nail component having at least one opening (14, 18) in its wall, and a fixation sleeve which has at least one opening (32) extending through it. One of the fixation sleeve and the nail component has a hollow bore so that the other of the sleeve and the nail component can be fitted within it in a coaxial sliding arrangement, with the openings in the wall of the nail component aligned with the openings in the fixation sleeve. A fixation pin (19) is inserted transversely through the openings in the wall of the nail component and the fixation sleeve when the said openings are aligned. An actuator (50) is used to cause the fixation sleeve to move axially relative to the nail component to cause a fixation pin inserted through the aligned openings in the nail component and the fixation sleeve to be gripped.

14 Claims, 5 Drawing Sheets

INTRAMEDULLARY NAIL ASSEMBLY

This invention relates to an intramedullary nail assembly.

Fractures of long bones (such as the humerus, femur and tibia) are commonly treated using an intramedullary nail. The bone fragments are held in alignment by means of a nail component which is inserted into the intramedullary canal. The nail component can be held in place by means of fixation pins which extend across the canal, extending through the bone tissue and through openings in the component. More than one fixation pin can be used, extending through openings in the nail component which are spaced apart, radially and axially.

The fixation pins are able to slide through the openings in the nail component. They are retained in their operating positions as a result of engaging the bone tissue. The fixation pins can become loose as a result of degradation of the bone tissue, for example if the tissue is osteoporotic. It is known to prevent loosening of a fixation pin which is close to an open end of the nail by means of an end cap inserted into an axially extending bore in the nail, so as to engage the pin. However, this cannot be used to secure fixation pins which are located other than close to the open end of the nail.

The present invention provides an intramedullary nail assembly which includes a fixation sleeve which can be fitted into the bore in the nail component, the fixation sleeve having at least one opening in its wall which can be aligned with an opening in the wall of the nail component.

Accordingly in one aspect, the invention provides an intraredullary nail assembly, which comprises:

a. a nail component which can be fitted into the medullary canal, the nail component having at least one opening in its wall allowing a pin to extend through the nail, b. a fixation sleeve which has at least one opening extending through it allowing a pin to extend through the sleeve, in which one of the fixation sleeve and the nail component has a hollow bore so that the other of the sleeve and the nail component can be fitted within it in a coaxial sliding arrangement, with the openings in the wall of the nail component aligned with the openings in the fixation sleeve, c. a fixation pin which can be inserted transversely through the openings in the wall of the nail component and the fixation sleeve when the said openings in the nail component and the fixation sleeve are aligned, and d. an actuator for causing the fixation sleeve to move axially relative to the nail component to cause a fixation pin inserted through the aligned openings in the nail component and the fixation sleeve to be gripped.

The nail assembly of the present invention has the advantage that fixation pins can be fastened against loosening. This can be achieved simultaneously when several fixation pins are used. Consequently, problems of fixation pins becoming loose, and possibly being displaced from within the nail component and aligned fixation sleeve, are reduced.

The fixation sleeve can be hollow along at least part of its length, so that the nail component can be received within it.

The nail component can hollow along at least part of its length, so that the fixation sleeve can be received within it.

Preferably, the cross-sections of the nail component and the fixation sleeve are non-circular so that angular displacement of one relative to the other is controlled. For example, one of the nail component and the fixation sleeve can have a tongue (or wing) can be received in a corresponding groove in the other of the nail component and fixation sleeve. Angular displacement can be controlled by means of at least one flat portion on one of the nail component and the fixation sleeve, with one or more corresponding flat portions on the other of the nail component and the fixation sleeve. For example, when the fixation sleeve fits into a bore in the nail component, the fixation sleeve can have be approximately D-shaped when viewed in cross-section, and the bore in the nail component can have a corresponding flat portion so that it is also approximately D-shaped.

Preferably, one of the nail component and the fixation sleeve has a longitudinal groove cut in its wall, and the other has a tongue (or wing) which can fit into the groove to slide along it when the nail component slides relative to the fixation sleeve, to control the relative angular displacement of the nail component and the fixation sleeve. The groove can extend through the entire thickness of the wall, especially when it is provided in the wall of the nail component, so that tongue on the fixation sleeve within the nail can be manipulated from outside the nail component. However, the groove need not extend through the entire thickness.

The fixation sleeve can be configured at its distal end to impinge on the pin that is furthest from the end of the nail at which the sleeve is fitted and that is intended to be locked by means of the sleeve. For example, the sleeve can be rounded at its distal end where it engages the said pin. When the fixation sleeve has a longitudinally extending bore, it can be closed at its distal end. For example, it can be closed by means of a plug which is inserted into the bore, especially which is rounded at its distal end. It can be preferred for the fixation sleeve to be closed at its distal end when it impinges on the furthest pin. However, there can be advantages of having the fixation sleeve open at its end, for example to facilitate the use of guide wires or other instrument components during the implantation procedure which extend along the axis of the nail component.

A fixation sleeve which is configured to engage a pin at its distal end can be configured to deform when placed under load. For example, slots can be formed in the wall of the sleeve to facilitate deformation, when placed under tension or, especially under a compressive load. Preferably, the deformation of the sleeve when placed under load (in tension or under compression) is resilient so that it can be at least partially recovered when the load is removed. This can help to ensure that loading on the fixation pins continues after it is initially applied.

Preferably, the actuator comprises a threaded cap. Preferably, one of the nail component and the fixation sleeve has a mating thread at or towards one end. The sleeve can then be made to move axially relative to the nail component by engaging the threaded cap with the thread on the fixation sleeve or the nail component.

The cap can have an enlarged head, with the thread on a shank which depends from the head. The head will be sized such that it does not fit into the bore which is provided in the fixation sleeve or the nail component. For example, the head can act against the end of the nail component when the shank is inserted into a bore in the nail component to engage a thread within the fixation sleeve, or it can act against the end of the fixation sleeve when the shank is inserted into a bore in the fixation sleeve to engage a thread within the nail component.

The thread on the plug can engage a thread within one of the nail or the sleeve, act at its distal end against the end of other of the nail and the sleeve. The plug can have a head which contacts the threaded nail or sleeve when the plug has been inserted sufficiently to deform the sleeve, to provide the surgeon with a end stop indication that this has been accomplished.

The actuator can cause the fixation sleeve to move along the nail component towards the actuator so that it contacts the fixation pin (or pins) on the surface thereof which faces away from the actuator and places the fixation sleeve under tension. The actuator can cause the fixation sleeve to move along the nail component in a direction away from the actuator so that it contacts the bone fixation pin (or pins) on the surface thereof which faces towards the actuator and places the fixation sleeve under compression.

Preferably, the nail component has at least first and second openings in its wall to allow pins to extend through the nail component at two different positions. Preferably, the first opening is offset radially relative to the second opening. Preferably, the first opening is offset along the axis of the nail component relative to the second opening. It is particularly preferred that the first opening in the nail component is offset relative to the second opening both radially and axially.

Preferably, the fixation sleeve has at least first and second openings in its wall. Preferably, the first of the openings in the sleeve is offset radially relative to the second of the said openings. Preferably, the first of the openings in the sleeve is offset along the axis of the sleeve relative to the second of the said openings. It is particularly preferred that the first of the said openings in the sleeve is offset relative to the second of the said openings both radially and axially.

The nail component or the fixation sleeve or both can have at least three openings, or at least four openings, or more. The selection of openings for the fixation pins can be made according to the location of a fracture in a patient's bone.

The actuator can comprise a fixation pin. A fixation pin can be used to cause the fixation sleeve to move axially relative to the nail component to cause that fixation pin and at least one other fixation pin to be gripped. This is possible when the nail and the fixation sleeve each have at least two openings in its wall, the openings being approximately aligned but with the spacing between them being slightly different. Alternatively, the fixation sleeve might rely on a fixation pin contacting it at its end, in which case the spacing between the end of the sleeve and the opening extending through the sleeve will be different from the spacing between the openings in the wall of the nail. When a fixation pin is used to cause relative movement between the fixation sleeve and the nail component, the deployment of the assembly might involve the following steps:

a. prepare bone cavity,
b. locate nail component in bone cavity,
c. prepare transverse screw holes in bone,
d. locate fixation sleeve in bore in nail component,
e. with openings for first fixation pin in bone, nail component and fixation sleeve aligned, insert first fixation pin through bone and nail component,
f. with openings for first fixation pin in bone and nail component aligned, but openings in fixation sleeve displaced slightly, insert second fixation pin through bone, causing relative movement between sleeve and nail component, so that the fixation sleeve grips the first and second fixation pins.

Preferably, the nail component is hollow and the bore extends along substantially its entire length, especially along its entire length. The bore can however be closed at one end, which will generally be the end which is inserted first into the intramedullary canal. When the nail component has a bore extending along part or all of its length, fixation openings will be provided in opposed pairs in the component's wall.

Preferably, the fixation sleeve has a bore which extends along at least part of its length. The bore can extend along the entire length of the fixation sleeve. When the fixation sleeve has a bore extending along part or all of its length, fixation openings will be provided in opposed pairs in the sleeve's wall. The provision of a bore in a fixation sleeve which is received in a bore in the nail component is particularly preferred when the fixation sleeve is formed from a metal because this can facilitate the formation of a secure connection between the fixation sleeve and one or more fixation pins, by deformation of the material of the sleeve or the pins or both. When the fixation sleeve is formed from a more deformable material such as certain polymers (especially UHMWPE), the fixation sleeve might not have a bore extending within it.

The openings in the nail component and the fixation sleeve will be arranged so that a fixation pin can pass through the nail component and the fixation sleeve generally transversely relative to the axis defined by the patient's intrameduuary canal, so that the fixation pins are fixed in the cancerous bone which defines the canal. The fixation pins need not be perpendicular to the said axis, although it can be preferred for the pins to be approximately perpendicular in many cases. For example, the openings can be arranged so that the angle between a pin inserted through the openings and the axis is not more than about 85°, or not more than about 80°, or not more than about 75°. The angle between the axis and a pin inserted through the first opening can be approximately the same as the angle between the axis and a pin inserted through the second pair of openings. The angle between the axis and a pin inserted through the first opening can differ from the angle between the axis and a pin inserted through the second opening.

It can be preferred for the openings, in the nail component or in the fixation sleeve or both, which engage the pins passing through the openings, to be arranged so that they are able to cut into the material of the pins when the fixation sleeve is made by the actuator to move axially within the bore in the nail component relative to the nail component. In this way, the grip on the pins by the cooperating nail component and fixation sleeve can be enhanced. For example, the edges of the openings can be sharpened; this can be achieved conveniently in both the nail component and the fixation sleeve when each of them is hollow, but is also possible when the fixation sleeve is not hollow. In addition, the material of the nail component or the fixation sleeve or both can be arranged to have a different hardness (so that can be harder or it can be softer) than the material of the fixation pin. A sleeve can be made from a titanium alloy or other metal which is less hard than a fixation pin when made from, for example certain stainless steels. The openings in the sleeve can be chamfered to facilitate deformation by the fixation pin. A sleeve can be made at least partially from a polymeric material which can be deformed. This can be particularly preferred in connection with a sleeve which has been configured to facilitate such deformation (for example by means of slits in an distal end portion, or by elongating the openings in the sleeve, or by providing at least one notch in the fixation sleeve around the openings for the fixation pin). A sleeve can be made as a composite, with a sleeve made from a polymeric material which has the openings formed in it for the fixation pin, and a core piece which has threads cut into it to engage the actuator.

The fixation sleeve can be configured in such a way that as to facilitate deformation where it contacts the fixation pins. For example, the openings in the fixation sleeve can be elongated so that they are approximately oval, being wider measured along the axis of the assembly than transverse to that axis. The fixation sleeve can be weakened at the sides of the openings to facilitate localised deformation when the sleeve is placed under tension. For example, the sleeve can have notches cut into it.

Preferably, the nail component has a threaded bore at its proximal end and in which the actuator comprises a plug with an external threaded shaft, and in which the threaded shaft on the plug can engage the thread in the bore of the nail component, allowing the actuator to be driven into the bore in the nail component so that its end engages the fixation sleeve and places it under compression.

Preferably, one of the nail component and the fixation sleeve has a longitudinal groove cut in its wall, and the other has a tongue which can fit into the groove to slide along it when the nail component slides relative to the fixation sleeve, to control the relative angular displacement of the nail component and the fixation sleeve. The components of the assembly can be made from materials which are used commonly in the manufacture of orthopaedic implants. Examples of suitable materials include certain stainless steels, and certain titanium based alloys. Particularly preferred materials include metals and metal alloys. For example, suitable materials include Ti6A17Nb and Ti6A14V alloys, certain stainless steels, and cobalt-chrome based alloys. Suitable polymeric materials include ultrahigh molecular weight polyethylene. Bioresorbable materials can be used, allowing controlled release of fixation pins after a predetermined period following implantation has elapsed.

Preferably, the transverse dimension (especially the diameter when the openings are circular) of the openings in the connector nail or in the fixation sleeve or both is only slightly greater than the transverse dimension of the fixation pin. For example, the ratio of the said diameters is preferably not more than about 1.5, more preferably not more than about 1.25, for example not more than about 1.1.

Embodiments of the invention will now be described by way of example with reference to the accompanying drawings, in which.

Figure 1:
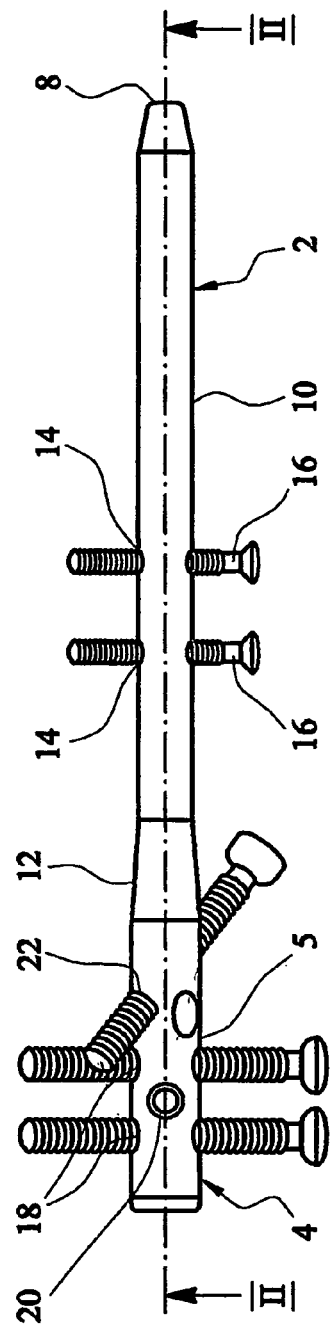
FIG. 1 is a side view of a nail assembly according to the invention.

Referring to the drawings, FIG. 1 shows a nail assembly which comprises a nail component 2 for location within the intramedullary cavity of a patient's long bone in the treatment of fractures. For example, the assembly can be used in a femur, or a humerus or a tibia. The nail component has a hollow bore at its proximal end 4. It is widest in the region 5 closest to the proximal end. The nail component is closed at its distal end 8 where it is tapered to facilitate insertion into the cavity. The nail component has a substantially constant cross-section over a large part 10 of its length between the distal end 8 and the wide region 4, with a tapered transition region 12.

In a preferred embodiment, the nail component has a substantially circular cross-section along its length. The diameter of the component in the distal region of constant cross-section is preferably at least about 5 mm, preferably not more than about 10 mm, for example about 8 mm. The diameter of the component in the proximal region of constant cross-section is preferably at least about 8 mm, preferably not more than about 15 mm, for example about 11 mm.

The nail component has a pair of through holes 14 in the constant cross-section region 10 in which distal fixation pins 16 can be received.

The nail component has a pair of through holes 18 in the wide region 4 which are approximately parallel to the through holes 14 in the constant cross-section region 10 in which proximal fixation pins 19 can be received. It has an additional through bore 20 which extends approximately perpendicular to the through holes 14 in the constant cross-section region 10. It has a further through bore 22 which extends at an angle of about 45° to the axis of the nail component and to the through holes 14 in the constant cross-section region.

The holes in the nail component will be sized to receive fixation pins without room for excessive play between the pins and the walls which define the holes. The diameter of the fixation pins might be for example at least about 2 mm, preferably at least about 3.5 mm. The diameter of the fixation pins will be not more than about 7.5 mm for many applications, preferably not more than about 5 mm. Different size fixation pins can be used in different parts of the assembly. For example, smaller fixation pins might be used distally compared with the pins which are used proximally, with corresponding sizing of the through holes in which the pins are received.

Figure 3:
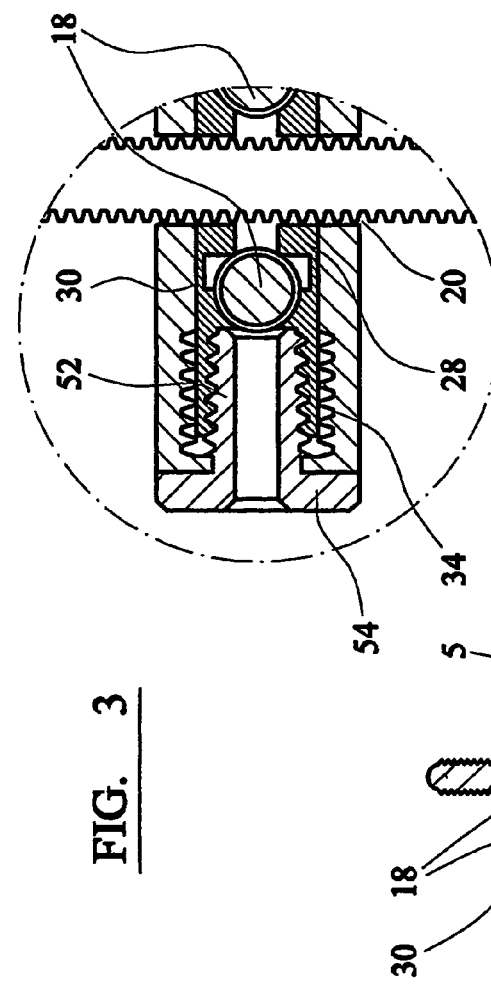
FIG. 3 is an enlarged view of the head of the nail assembly shown in FIG. 2.
Figure 2:
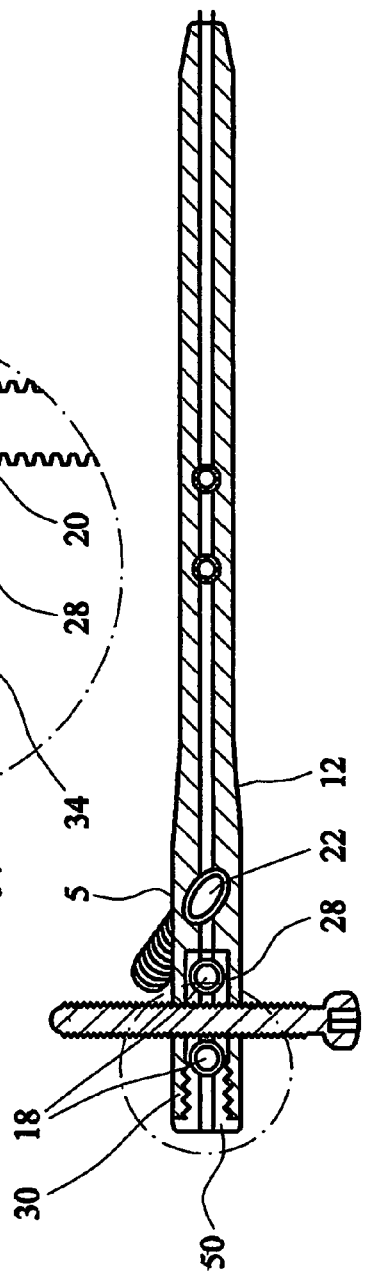
FIG. 2 is a cross-section through the nail assembly shown in FIG. 1, along the line II-II.
Figure 4:
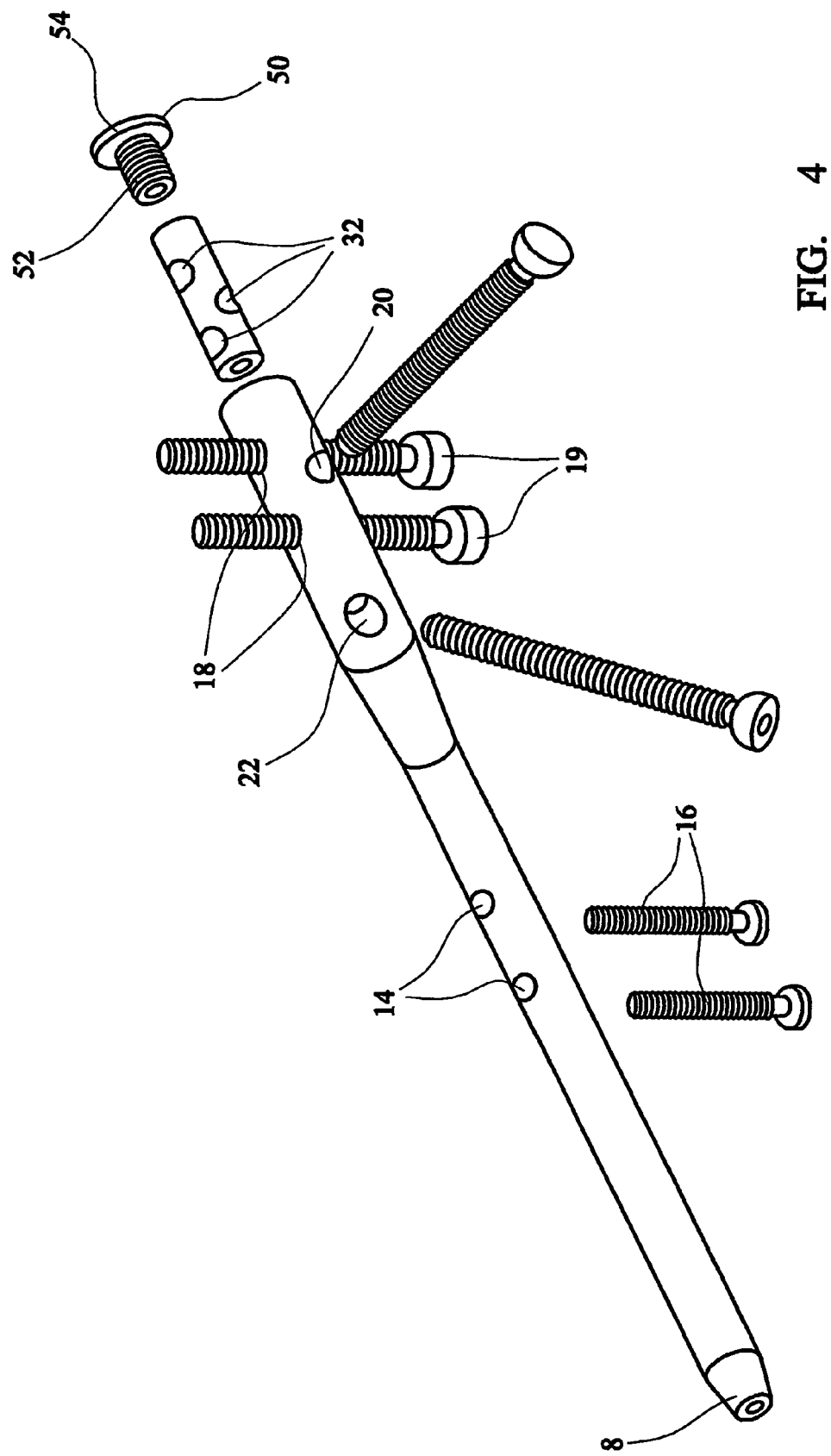
FIG. 4 is an exploded isometric view of the nail assembly shown in FIG. 1, with additional fixation pins.
Figure 5A:
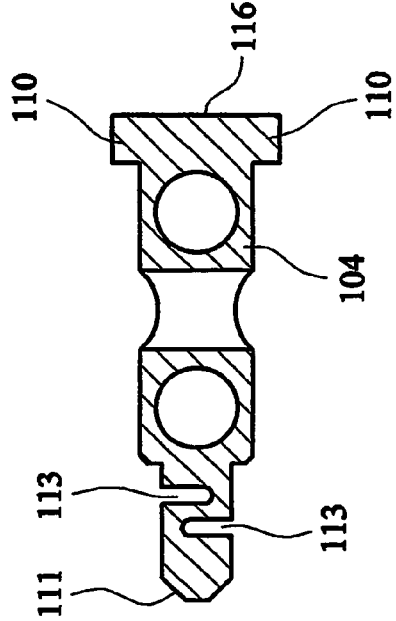
FIGS. 5a, 5b and 5c are sectional elevations through the fixation sleeve, end cap and nail components of another embodiment of nail assembly.
Figure 5A:
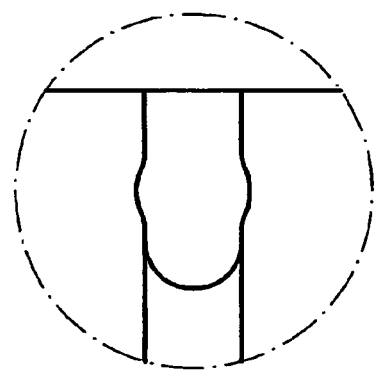
Figure 5A:
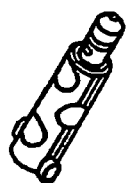
Figure 5B:
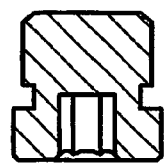
Figure 5B:
Figure 5C:
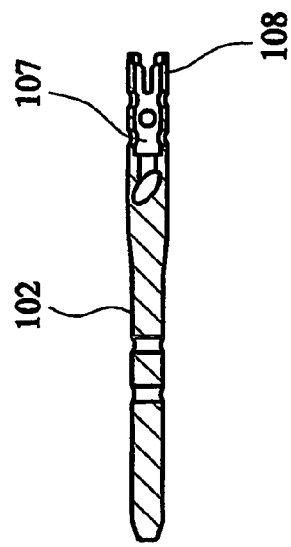
Figure 5C:
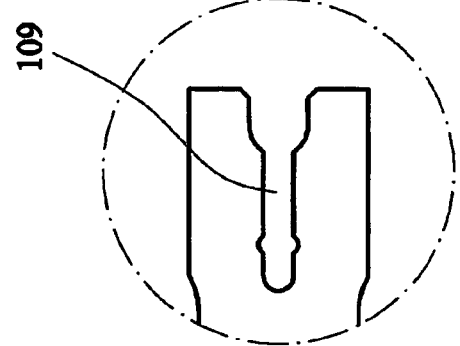
Figure 5C:

As shown in FIGS. 2 to 4, a fixation sleeve 28 is received in the hollow bore 30 in the proximal region 4 of the nail component. The fixation sleeve is hollow and has three through holes 32 extending through it. These holes are positioned so that they can be aligned with the holes 18 which are parallel to the holes 14 in the distal constant cross-section region, and with the hole 20 which is perpendicular to the holes 14 in the distal constant cross-section region, so that a fixation pin can be inserted through the aligned holes in the fixation sleeve and the nail component.

The fixation sleeve is hollow and has an internal thread 34 at one end. It is formed from a metal which is softer than the metal of the fixation pins (for example titanium or a titanium alloy) or from a polymer (such as ultra high molecular weight polyethylene).

The assembly includes an end cap 50 which has a shank portion 52 with an external thread and a head 54.

In use, a bone is prepared to receive the fixation assembly by reaming the intramedullary cavity using reamers of appropriate size having regard to the diameters of the nail component in the distal and proximal regions.

The nail assembly is assembled by locating the fixation sleeve 28 in the bore 30 in the nail component, with the holes in the two parts aligned. The fixation sleeve is retained in place in the bore by means of the end cap whose shank portion 52 threadingly engages the fixation sleeve, and whose head 54 abuts the end of the nail component.

The selection of locations for fixation pins will be determined in the pre-operative planning stage of the surgical procedure, using images (especially X-ray images) which reveal the nature and location of the fractures. The patient's bone is prepared to receive fixation pins using appropriate guide tools by drilling. Tools of this general kind exist. Examples of tools of the general kind are disclosed in EP-A-321170 and U.S. Pat. No. 5,403,321.

Pins can be inserted through the drilled holes in the bone and the holes in the nail component, and through the aligned holes in the fixation sleeve in the case of the fixation sleeve at the proximal end of the nail component.

The pins at the proximal end of the nail component can be locked in place by moving the fixation sleeve in the bore in the nail component axially relative to the nail component by rotating the end cap. Depending on the direction of rotation of the end cap, this will cause the fixation sleeve to advance deeper into the bore, or to be withdrawn out of the bore. Such displacement cases the fixation pins which pass through the nail component to be gripped in the shearing action on the pins of the holes in the nail component and the fixation sleeve respectively.

Any inaccuracy in the location of the fixation pins, which causes one of the pins to be gripped by this shearing action before the other(s) of the pins are gripped, is accommodated by deformation of the material of the fixation sleeve.

The material of the fixation sleeve can be bioresorbable, allowing the fixation pins to be freed from within the nail component for removal after the fracture in the bone has healed.

FIG. 5 shows components of another embodiment of nail assembly. This assembly also comprises a nail component 102, a fixation sleeve 104 and an end cap 106. The nail component has a bore 107 at its proximal end 108, and a pair of slots 109 cut into the wall which defines the bore. The bore 107 in the nail component is threaded at its proximal end.

The fixation sleeve has a pair of outwardly directed tongues 110 which can slide in the slots. The location of the tongues in the slots helps to maintain appropriate alignment of the holes in the fixation sleeve and the nail component.

The fixation sleeve is closed at its distal end 111, which is generally rounded where it is intended to impinge on the pin that is furthest from the end of the nail at which the sleeve is fitted. A plurality of slits 113 are provided towards the distal end of the sleeve to facilitate compression of the sleeve. The fixation sleeve can however be open at its distal end, for example as a result of formation from a tube.

The openings 115 in the fixation sleeve can be configured to facilitate deformation when placed under a compressive load. For example, the openings can be slightly elongated. The openings can have notches at each side.

The end cap 106 has a shank portion 112 which bears an external thread. Its end face 114 bears against the end face 116 of the fixation sleeve, so as to force the fixation sleeve deeper into the bore. The end cap is driven against the end face of the fixation sleeve by engagement between the external thread on the shank portion of the end cap and the internal thread in the bore in the end of the nail component. This causes the sleeve to deform under a compressive load due to contact with each of the fixation pins which extend through the nail component at its proximal end. This deformation is facilitated by the slits 113 at the distal end of the sleeve, and by the elongation of the holes in the fixation sleeve and the notches which communicate with the holes.

Figures 6A, 6B:
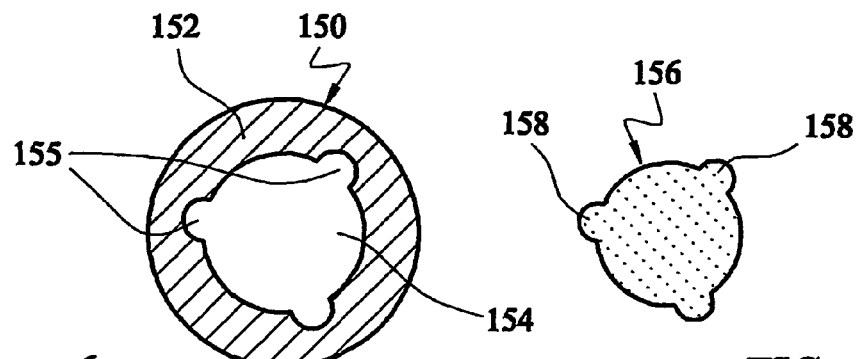
FIGS. 6a and 6b are sectional elevations through a fixation sleeve and a nail component of another embodiment of nail assembly.

FIG. 6a is a cross-section through the proximal region of a nail component 150 according to the invention, showing the wall 152 of the nail component which defines a bore 154 within it. The bore is generally circular in cross-section, with three grooves 155 which are spaced apart uniformly around the bore. FIG. 6b is a cross-section through a fixation sleeve 156 which can be positioned in the bore 154 in the nail component, and used to anchor fixation pins which extend transversely across the nail component, generally as described above in relation to FIGS. 1 to 5. The fixation sleeve is generally circular in cross-section, with three extending outwardly lugs 158. The cross-sectional shape of the fixation sleeve with its outwardly extending lugs corresponds to the cross-sectional shape of the bore in the nail component, so that the fixation sleeve can fit into the bore in the nail component. When the lugs 158 are received in the grooves 155, the sleeve is held against rotation relative to the bore in the nail component.

Figures 7A, 7B:
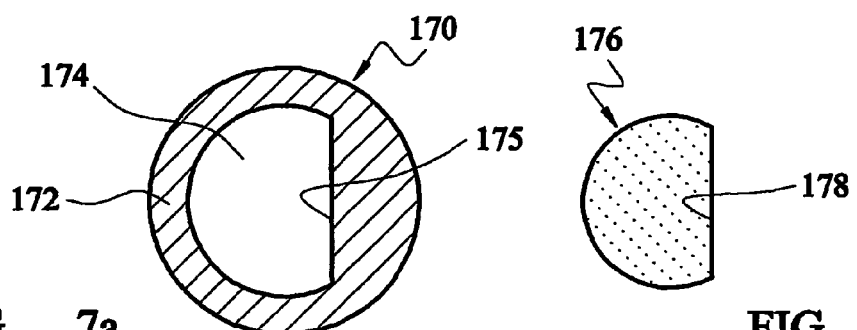
FIGS. 7a and 7b are sectional elevations through a fixation sleeve and a nail component of another embodiment of nail assembly.

FIG. 7a is a cross-section through the proximal region of a nail component 170 according to the invention, showing the wall 172 of the nail component which defines a bore 174 within it. The bore is generally circular in cross-section, with a flat portion 175 in one part of its wall. FIG. 7b is a cross-section through a fixation sleeve 176 which can be positioned in the bore 174 in the nail component, and used to anchor fixation pins which extend transversely across the nail component, generally as described above in relation to FIGS. 1 to 5. The fixation sleeve is generally circular in cross-section, with a flat portion 178 in one part of its wall. The cross-sectional shape of the fixation sleeve with its flat portion 178 corresponds to the cross-sectional shape of the bore in the nail component, so that the fixation sleeve can fit into the bore in the nail component. When the flat portion 178 of the wall of the fixation sleeve is positioned against the flat portion 175 of the wall of the bore, the sleeve is held against rotation relative to the bore in the nail component.

Figure 8:
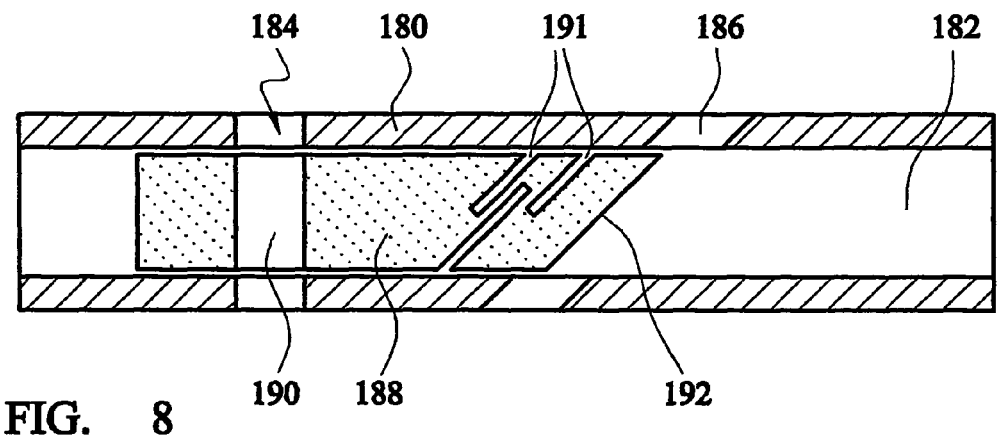
FIG. 8 is a sectional elevation through a fixation sleeve and nail component of another embodiment of nail assembly.

FIG. 8 shows the proximal portion 180 of a nail component which has a bore 182 formed in it, extending along its length. First and second openings 184, 186 are formed in the nail component, communicating with the bore 182 therein. The first opening extends across the nail, perpendicular to the axis of the nail. The second opening is arranged at an inclined angle to the axis.

A fixation sleeve 188 is provided in the bore in the nail. The fixation sleeve has an opening 190 formed in it, extending perpendicular to the axis of the sleeve. The sleeve has a plurality of slits 191 formed in its wall which allow the sleeve to be compressed longitudinally. The sleeve is formed from a material which enables the compression to be recovered at least partially. The angle between one of the ends 192 of the sleeve and the axis is about the same as the angle between the second opening 186 in the wall of the nail component and the axis of the nail component. The distance between the opening 190 in the fixation sleeve and the inclined end 192 of the sleeve is slightly greater than the distance between the first and second openings 184, 186 in the nail component.

In use, a first fixation pin (which will often be a fixation screw) is inserted through the first opening 184 in the nail and the opening 190 in the fixation sleeve. A second fixation pin is inserted through the second opening 186 in the nail. When the fixation pin is inserted into the second opening in the nail, it acts against the inclined end 192 of the fixation sleeve and causes the fixation sleeve to be compressed longitudinally, between the first and second fixation pins. The action of the fixation sleeve against the fixation pins causes them to be gripped in the nail component.

Figure 9:
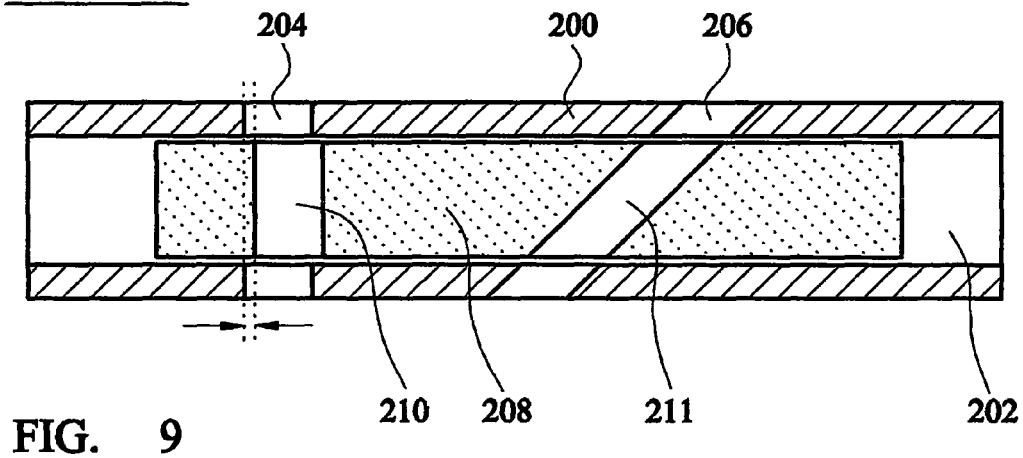
FIG. 9 is a sectional elevation through a fixation sleeve and nail component of another embodiment of nail assembly.

FIG. 9 shows the proximal portion 200 of a nail component which has a bore 202 formed in it, extending along its length. First and second openings 204, 206 are formed in the nail component, communicating with the bore 202 therein. The first opening extends across the nail, perpendicular to the axis of the nail. The second opening is arranged at an inclined angle to the axis.

A fixation sleeve 208 is provided in the bore in the nail. The fixation sleeve has first and second openings 210, 211 formed in it. The first opening 210 extends perpendicular to the axis of the sleeve. The second opening 211 is inclined to the axis of the sleeve, with the angle between the second opening in the fixation sleeve and the axis of the sleeve about the same as the angle between the second opening 186 in the wall of the nail component and the axis of the nail component. The distance between the first and second openings 210, 211 in the fixation sleeve is slightly greater than the distance between the first and second openings 204, 206 in the nail component. The fixation sleeve is made from a deformable material, such as a polymeric material (especially UHMWPE) or a metal which is softer than the metal of the fixation pins which are contemplated for use.

In use, a first fixation pin (which will often be a fixation screw) is inserted through the first opening 204 in the nail and the opening 210 in the fixation sleeve. A second fixation pin is inserted through the second opening 206 in the nail and the second opening 211 in the fixation sleeve. The difference between the distances between the first and second openings in the sleeve and the nail component respectively means that the fixation sleeve is deformed as a result of the pulling forces exerted on it by the first and second fixation pins.

Figure 10:
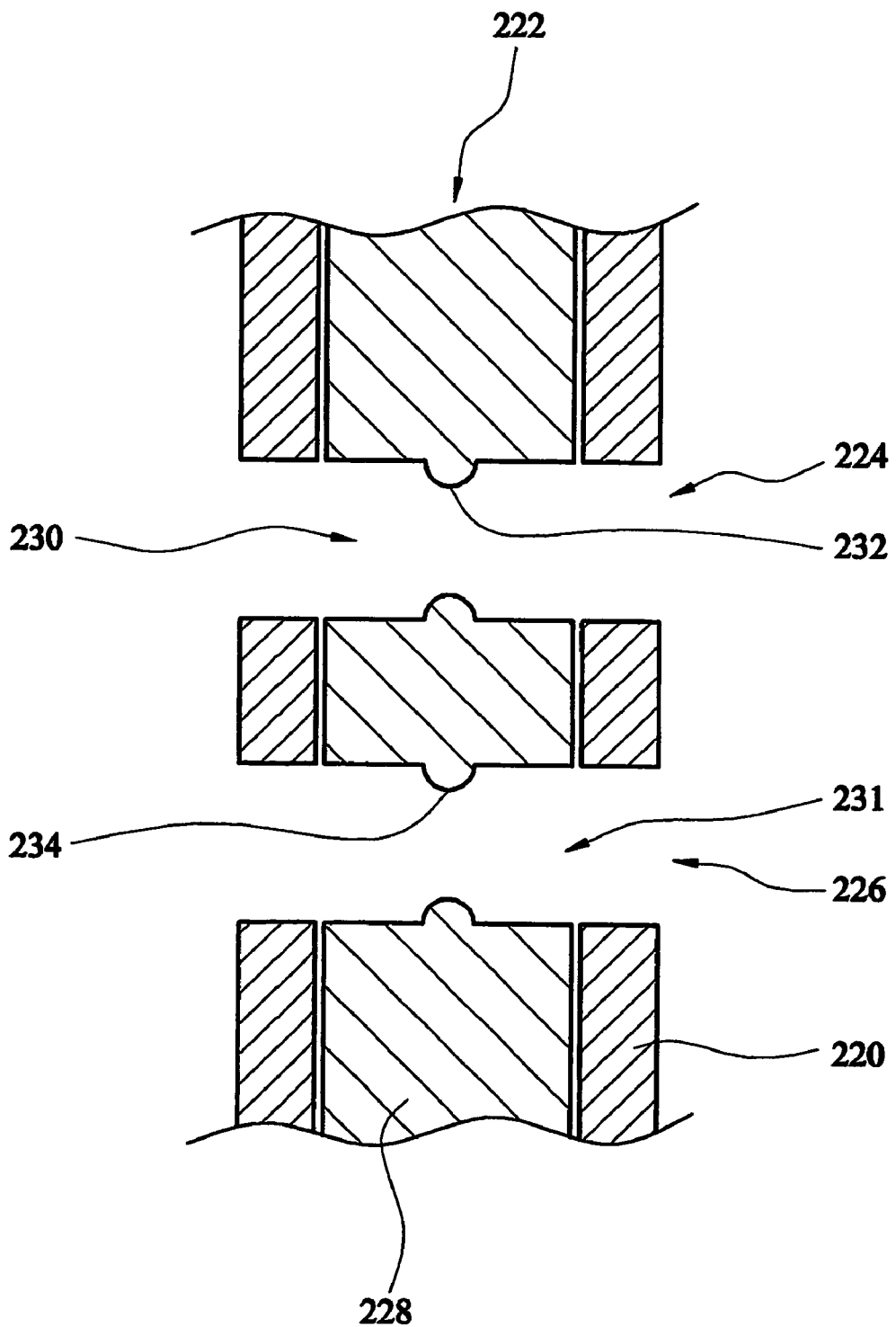
FIG. 10 is a sectional elevation through a fixation plug and nail component of another embodiment of nail assembly.

FIG. 10 shows the proximal portion 220 of a nail component which has a bore 222 formed in it, extending along its length. First and second openings 224, 226 are formed in the nail component, communicating with the bore 222 therein. The first and second openings extend across the nail, perpendicular to the axis of the nail.

A fixation plug 228 is provided in the bore in the nail. The fixation plug has first and second openings 230, 231 formed in it. The first and second openings extend across the plug, perpendicular to the axis of the plug. The distance between the first and second openings 230, 231 in the fixation plug is slightly greater than the distance between the first and second openings 224, 226 in the nail component. The fixation plug can be made from a deformable material, such as a polymeric material (especially UHMWPE). Each of the openings 230, 231 in the fixation plug has a protrusion 232, 234 formed in it, so that the openings are narrowed locally. The protrusion can be in the form of a ring that extends around the interior of the opening in the plug.

The assembly shown in FIG. 10 is used with a fixation pin (which will often be a fixation screw) which is slightly wider than the distance across the openings in the fixation plug, measured at the protrusions 232, 234. Accordingly, as the fixation pin is inserted through the openings in the nail component and the fixation plug, the material of the fixation plug is deformed locally at the protrusions.

While the embodiments shown in the drawings have a bore in the nail component in which the fixation sleeve is received, the reverse arrangement is envisaged in which the fixation sleeve has a bore within it, in which the proximal part of the nail component is received.

The invention claimed is:

1. An intramedullary nail assembly for use in a medullary canal, comprising:
 a nail component configured to fit into the medullary canal, the nail component having a hollow bore and comprising a wall having a first wall opening and a second wall opening, the first wall opening and the second wall opening being spaced apart axially by a first distance;
 a sleeve comprising a sleeve wall having at least a first sleeve opening and a deformable portion, and wherein the nail component has a hollow bore and at least the deformable portion of the sleeve is configured to be disposed within the hollow bore in a sliding arrangement, the deformable portion having a first, undeformed length that is longer than the first distance and is configured to be deformed by a defined force to a second length that is approximately equal to the first distance;
 a first fixation pin sized and configured to be inserted transversely through the first wall opening and the first sleeve opening when the first wall opening and the first sleeve opening are approximately aligned;
 a second fixation pin sized and configured to be inserted transversely through the second wall opening, the sleeve and nail component being configured such that, when the first fixation pin is inserted through the first wall opening and the first sleeve opening, and the second fixation pin is inserted through the second wall opening, the deformable portion of the sleeve is deformed to the second length.

2. The nail assembly of claim 1, wherein one end of the deformable portion of the sleeve is formed by the first sleeve opening.

3. The nail assembly of claim 2, wherein the second end of the deformable portion of the sleeve is formed by the second sleeve opening.

4. The nail assembly of claim 2, wherein the sleeve has a distal end and the second end of the deformable portion of the sleeve is formed by the distal end.

5. The nail assembly of claim 1, wherein the deformable portion comprises at least one slit.

6. The nail assembly of claim 5, wherein the deformable portion comprises a plurality of slits.

7. The nail assembly of claim 1, wherein the deformable portion is at least partially comprised of a deformable material.

8. The nail assembly of claim 1, wherein the sleeve comprises a distal end and the second fixation pin bears on the distal end when the second fixation pin is inserted transversely through the second wall opening.

9. The nail assembly of claim 1, wherein the sleeve comprises a second sleeve opening sized configured to accept the second fixation pin, and wherein the second fixation pin bears on the inner surface of the second sleeve opening when the second fixation pin is inserted transversely through the second wall opening and the second sleeve opening.

10. The nail assembly of claim 9, wherein the first sleeve opening is offset along the axis of the nail component relative to the second sleeve opening.

11. The nail assembly of claim 1, wherein the first wall opening is offset along the axis of the nail component relative to the second wall opening.

12. The nail assembly of claim 1, further comprising an actuator for causing the sleeve to move axially relative to the nail component.

13. The nail assembly of claim 12, wherein the actuator comprises a cap, and wherein the sleeve is configured to move axially within the bore in the nail component when the cap engages with the sleeve.

14. The nail assembly of claim 1, wherein one of the nail component and the fixation sleeve has a longitudinal groove cut in its wall, and the other has a tongue configured to fit into the groove to slide along the groove when the nail component slides relative to the fixation sleeve.

* * * * *

UNITED STATES PATENT AND TRADEMARK OFFICE
CERTIFICATE OF CORRECTION

PATENT NO. : 7,763,021 B2  
APPLICATION NO. : 10/557164  
DATED : July 27, 2010  
INVENTOR(S) : Dean J. Cole et al.

Page 1 of 2

It is certified that error appears in the above-identified patent and that said Letters Patent is hereby corrected as shown below:

Column 1,  
Line 59, after "can" insert --be--

Column 1,  
Line 65, after "(or wing)" insert --that--

Column 2,  
Line 5, after "can" delete "have"

Column 2,  
Line 16, after "so that" insert --the--

Column 2,  
Line 66, replace "a end stop" with --an end stop--

Column 3,  
Line 45, after "a" insert --.--

Column 4,  
Line 17, replace "intrameduuary" with --intramedullary--

Column 4,  
Line 18, replace "cancerous" with --cancellous--

Column 4,  
Line 46, after "that" insert --it--

Column 4,  
Line 55, replace "an distal" with --a distal--

Signed and Sealed this  
Nineteenth Day of February, 2013

Teresa Stanek Rea  
*Acting Director of the United States Patent and Trademark Office*

CERTIFICATE OF CORRECTION (continued)
U.S. Pat. No. 7,763,021 B2

Column 4,
Line 62, after "way" delete "that"

Column 7,
Line 16, replace "cases" with --causes--